US012714818B2

(12) United States Patent
Yoshida et al.

(10) Patent No.: US 12,714,818 B2
(45) Date of Patent: Aug. 25, 2026

(54) TRACHEAL CONNECTOR WITH A FLOW RESTRICTIVE MECHANISM

(71) Applicants: OSAKA UNIVERSITY, Suita (JP); NIHON KOHDEN CORPORATION, Tokyo (JP)

(72) Inventors: Takeshi Yoshida, Suita (JP); Shigeo Wada, Suita (JP); Naoki Takeishi, Suita (JP); Satoshi Yasumura, Tokorozawa (JP); Isao Matsubara, Tokorozawa (JP)

(73) Assignees: OSAKA UNIVERSITY, Osaka (JP); NIHON KOHDEN CORPORATION, Tokyo (JP)

( * ) Notice: Subject to any disclaimer, the term of this patent is extended or adjusted under 35 U.S.C. 154(b) by 826 days.

(21) Appl. No.: 18/070,991

(22) Filed: Nov. 29, 2022

(65) Prior Publication Data

US 2023/0173212 A1 Jun. 8, 2023

(30) Foreign Application Priority Data

Dec. 6, 2021 (JP) ................................ 2021-197705

(51) Int. Cl.
*A61M 16/08* (2006.01)
*A61M 16/04* (2006.01)

(52) U.S. Cl.
CPC .... *A61M 16/0816* (2013.01); *A61M 16/0463* (2013.01)

(58) Field of Classification Search
CPC .......... A61M 16/0816; A61M 16/0875; A61M 16/0406; A61M 2206/10; A61M 2016/0033; A61M 2016/0039
See application file for complete search history.

(56) References Cited

U.S. PATENT DOCUMENTS 9,539,401 B2 * 1/2017 Tatkov .............. A61M 16/0833
10,441,739 B1 * 10/2019 Golub .................. A61M 16/20
(Continued)

FOREIGN PATENT DOCUMENTS

JP 11 276589 A 10/1999
JP 2008 161528 A 7/2008
JP 3182554 U 4/2013

OTHER PUBLICATIONS

Office Action dated Apr. 15, 2025 issued by the Japan Patent Office in Japanese Patent Application No. 2021-197705.

*Primary Examiner* — Brandy S Lee
*Assistant Examiner* — Sydney Reyes Russell
(74) *Attorney, Agent, or Firm* — Sughrue Mion, PLLC

(57) ABSTRACT

A tracheal connector is connected to a respiratory gas generator and a tracheal tube. The tracheal connector includes a tracheal connector body connected to the tracheal tube, a connector tube connected to the tracheal connector body and the respiratory gas generator, and a restriction mechanism configured to narrow a respiratory gas flow path configured to allow the respiratory gas to flow therein. The tracheal connector body includes a tracheal port connected to the tracheal tube, an exhaust port facing the tracheal port and configured to discharge at least expired air of the subject, and a respiratory port connected to the connector tube. The restriction mechanism is provided on the respiratory gas flow path between the respiratory port and the tracheal port.

5 Claims, 4 Drawing Sheets

(56) References Cited

U.S. PATENT DOCUMENTS

| | | | | |
|---|---|---|---|---|
| 12,133,956 | B2 * | 11/2024 | Kemps .............. | A61M 16/0875 |
| 2012/0272954 | A1 | 11/2012 | Landis et al. | |
| 2013/0081616 | A1 | 4/2013 | Tatkov | |
| 2017/0113012 | A1 | 4/2017 | Tatkov | |
| 2020/0179637 | A1 | 6/2020 | Tatkov | |
| 2022/0409842 | A1 | 12/2022 | Tatkov | |
| 2024/0024603 | A1 * | 1/2024 | White ................ | A61M 16/208 |
| 2024/0024608 | A1 * | 1/2024 | Mcdermott ....... | A61M 16/1095 |

* cited by examiner

TRACHEAL CONNECTOR WITH A FLOW RESTRICTIVE MECHANISM

CROSS-REFERENCE TO RELATED APPLICATIONS

The present application claims the benefit of priority of Japanese Patent Application No. 2021-197705, filed on Dec. 6, 2021, the content of which is incorporated herein by reference.

TECHNICAL FIELD

The present disclosure relates to a tracheal connector. In particular, the present disclosure relates to a tracheal connector connected to a respiratory gas generator and a tracheal tube.

BACKGROUND

Among patients requiring mechanical ventilation for two-~three weeks, most (about 90%) are subjected to be tracheotomized, followed by the attempt to wean from a mechanical ventilator. It has been found that tracheostomized patients that have weaned from a mechanical ventilator has improved long-term prognosis as compared with tracheostomized patients dependent on the mechanical ventilator. Specifically, the data indicates that the survival rate after three years of tracheostomized patients that have weaned from a mechanical ventilator is 60%, whereas the survival rate after three years of tracheostomized patients dependent on the mechanical ventilator is 30%. In addition, early weaning from a mechanical ventilator also contributes to a significant reduction in the medical cost (about ⅙). In this way, it is preferable that patients after tracheotomy can wean from a mechanical ventilator as soon as possible. The main reason for difficult weaning from a mechanical ventilator is two points, i.e., impaired capacity of gas exchange and reduced endurance capacity of respiratory muscle to increased work of breathing. In currently available tracheal connectors that connect a respiratory gas generator and a tracheal tube inserted into the trachea of a patient, a positive airway pressure during expiration (hereinafter, referred to as dynamic positive end expiratory pressure (PEEP)) is lowered. As a result, the alveoli of the patient may collapse, leading to difficult wearing from the mechanical ventilator. Therefore, if it is possible to generate a positive airway pressure during expiration by improving the current tracheal connector, it is expected to decrease the alveolar collapse and improve the gas exchange. As a result, the end-expiratory lung volume is increased and the work of breathing (respiratory effort) is reduced, thereby promoting early weaning from a mechanical ventilator.

On the other hand, in the tracheal connector disclosed in U.S. Pat. No. 9,539,401, a part of the structure of the tracheal connector is devised to generate a dynamic PEEP of a certain amount. Specifically, a restriction mechanism of a flow path having a through orifice is formed on the side closer to the exhaust port of the tracheal connector. Since the air flow of the expired air of the patient (expiratory flow) is less likely to be smoothly exhausted into the atmosphere due to the restriction mechanism, the value of the dynamic PEEP of the patient tends to increase easily. In this way, since the alveolar collapse of the patient is suitably prevented as the value of the dynamic PEEP of the patient increases, the wearing period of the respirator of the patient may be shortened.

Incidentally, in the tracheal connector disclosed in U.S. Pat. No. 9,539,401, since the restriction mechanism of the flow path is formed on the side closer to the exhaust port of the tracheal connector, it is assumed that the phlegm or the like mixed with the expired air of the patient blocks a part of the through orifice. In such a situation, since the expiratory flow is less likely to be discharged smoothly into the atmosphere, the value of the dynamic PEEP is dramatically increased, which may cause a problem in the respiratory management of the patient. From the above viewpoint, there is room for further improvement of the tracheal connector.

SUMMARY

The present disclosure is provided with a tracheal connector capable of suitably preventing insufficient discharge of the expired air of a subject into the atmosphere while dramatically improving the value of the dynamic PEEP of the subject.

An aspect of the present disclosure of a tracheal connector is connected to a respiratory gas generator configured to supply a respiratory gas to a subject and a tracheal tube inserted into a trachea of the subject, in which the tracheal connector includes
- a tracheal connector body connected to the tracheal tube,
- a connector tube connected to the tracheal connector body and the respiratory gas generator,
- a respiratory gas flow path configured to flow the respiratory gas therein; and
- a restriction mechanism configured to narrow the respiratory gas flow path so that a flow of the respiratory gas is restricted and accelerates, the tracheal connector body includes
- a tracheal port connected to the tracheal tube,
- an exhaust port facing the tracheal port and configured to discharge at least expired air of the subject, and
- a respiratory port connected to the connector tube, and the restriction mechanism of the flow path is provided on the respiratory gas flow path between the respiratory port and the tracheal port.

According to the above configuration, since the restriction mechanism of the flow path configured to narrow the respiratory gas flow path is arranged on the respiratory gas flow path between the respiratory port and the tracheal port, the flow of the respiratory gas (hereinafter, the inspiratory flow) supplied from the respiratory gas generator is restricted by the restriction mechanism of the flow path. Further, when the inspiratory flow passing through the restriction mechanism of the flow path collides with the flow of the expired air of the subject passing through the tracheal port (hereinafter referred to as an expiratory flow), a turbulent flow region is formed in the vicinity of the tracheal port. Therefore, the expiratory flow is less likely to flow smoothly toward the side closer to the exhaust port, and thus the pressure in the vicinity of the tracheal port increases. As a result, the value of the dynamic PEEP (positive end expiratory pressure) dramatically increases. Further, the restriction mechanism of the flow path is not provided on the side closer to the exhaust port. Therefore, the restriction mechanism of the flow path can suitably prevent the expired air of the subject from being not sufficiently discharged into the atmosphere. Therefore, it is possible to provide a tracheal connector capable of suitably preventing insufficient discharge of the expired air of a subject into the atmosphere while dramatically improving the value of the dynamic PEEP of the subject.

According to the present disclosure, it is possible to provide a tracheal connector capable of suitably preventing insufficient discharge of the expired air of a subject into the atmosphere while dramatically improving the value of the dynamic PEEP of the subject.

DESCRIPTION OF EMBODIMENTS

Figure 1:
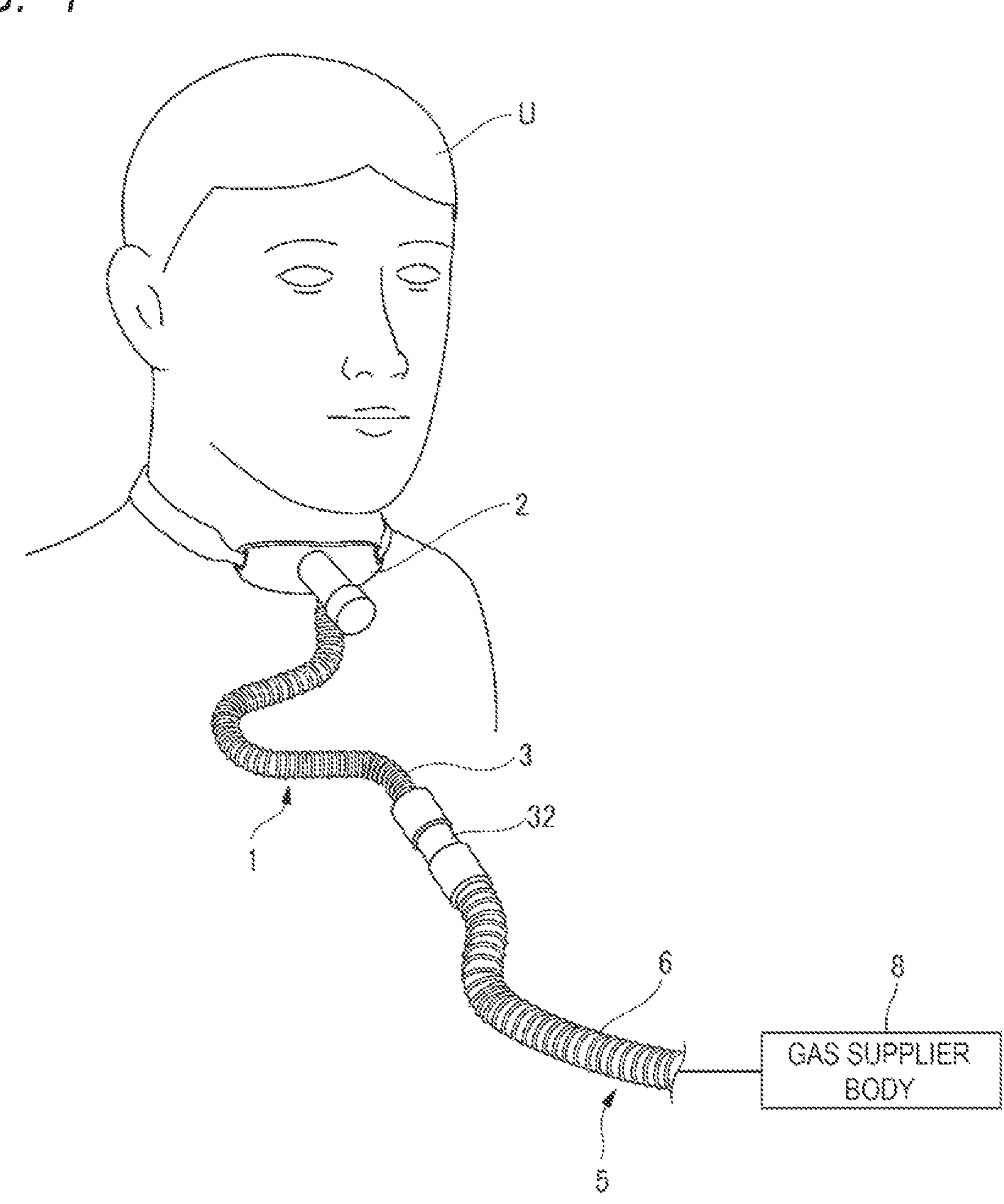
FIG. 1 is a perspective view illustrating a state in which a tracheal connector according to an embodiment of the present disclosure is attached to a patient.
Figure 2:
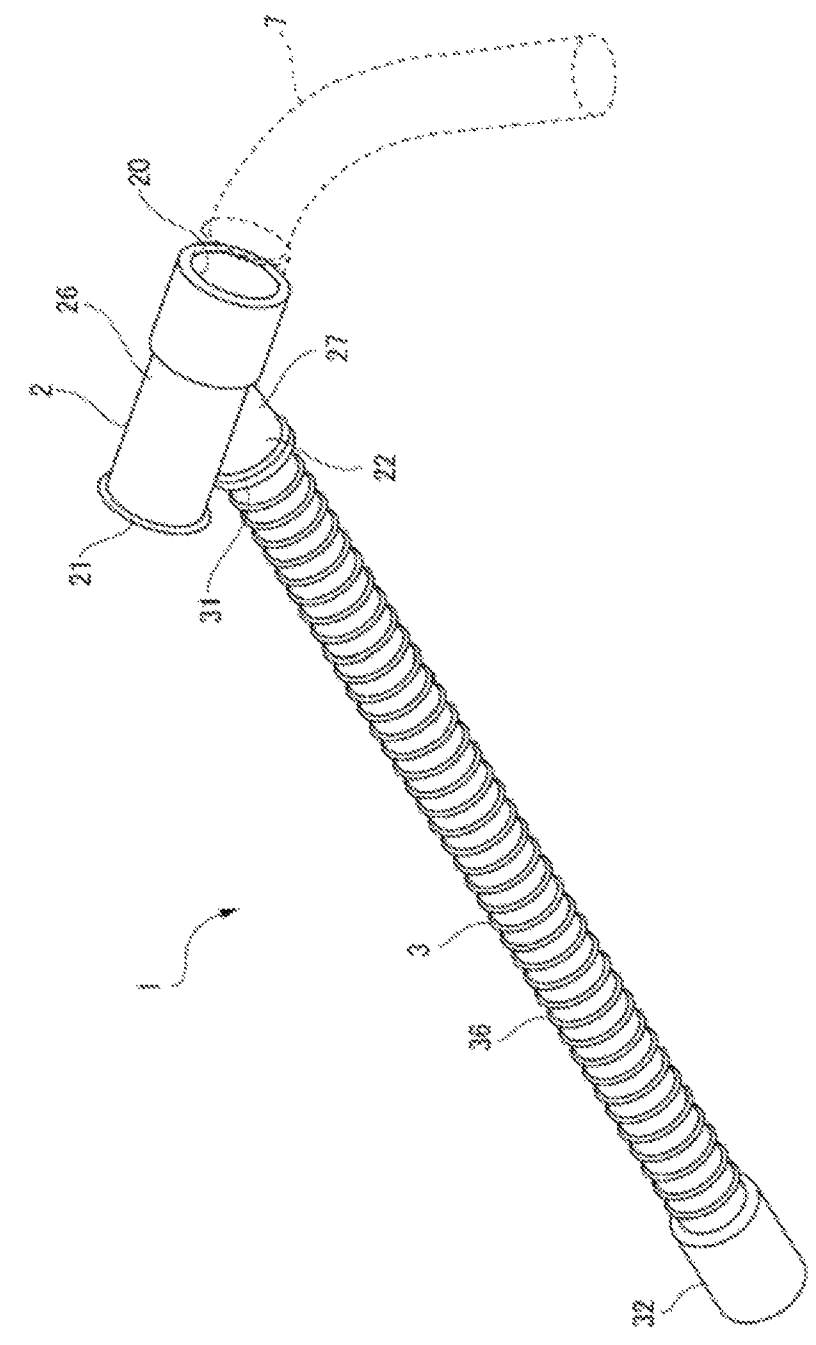
FIG. 2 is a perspective view of the tracheal connector.

A tracheal connector 1 according to an embodiment of the present disclosure (hereinafter, the present embodiment) will be described below with reference to the drawings. FIG. 1 is a perspective view illustrating a state in which the tracheal connector 1 according to the present embodiment is attached to a patient U (subject). FIG. 2 is a perspective view of the tracheal connector 1. As illustrated in FIG. 1, the patient U is a patient who needs respiration support after tracheotomy. In particular, the trachea of the patient U is incised, and a tracheal tube 7 (see FIG. 2) is inserted into the trachea. The respiratory gas (e.g., oxygen gas) supplied from a respiratory gas generator 5 is fed into the trachea of the patient U via the tracheal connector 1 and the tracheal tube 7. On the other hand, the expired air, discharged from the lungs of the patient U and containing carbon dioxide, is discharged into the atmosphere through the tracheal tube 7 and an expiratory port 21.

As illustrated in FIG. 1, the respiratory gas generator 5 is connected to the tracheal connector 1. The respiratory gas generator 5 is configured to supply the respiratory gas to the patient U. The respiratory gas generator 5 may include a gas generator body 8 configured to supply the respiratory gas to the patient U via the tracheal connector 1, and a gas tube 6 connected to the gas generator body 8.

As illustrated in FIGS. 1 and 2, the tracheal connector 1 is connected to the gas tube 6 of the respiratory gas generator 5 and the tracheal tube 7. The tracheal connector 1 may include a tracheal connector body 2 and a connector tube 3. The tracheal connector body 2 is connected to the tracheal tube 7, and may include a tracheal port 20, an exhaust port 21, and a respiratory port 22. The tracheal port 20 is connected to the tracheal tube 7. The exhaust port 21 faces the tracheal port 20. The expired air discharged from the patient U and passing through the tracheal tube 7 is discharged to the outside from the exhaust port 21 via the tracheal port 20. The respiratory port 22 is connected to the connector tube 3. The respiratory gas output from the respiratory gas generator 5 passes through the respiratory port 22 and the tracheal port 20, and then is fed into the trachea of the patient U via the tracheal tube 7. Further, a part of the respiratory gas is discharged to the outside from the exhaust port 21.

The tracheal connector body 2 may further include an exhaust-side tube portion 26 and a respiratory-side tube portion 27. The exhaust-side tube portion 26 extends between the tracheal port 20 and the exhaust port 21. The respiratory-side tube portion 27 is connected to the exhaust-side tube portion 26 and has the respiratory port 22. The respiratory-side tube portion 27 and the exhaust-side tube portion 26 may be formed integrally.

Figure 3:
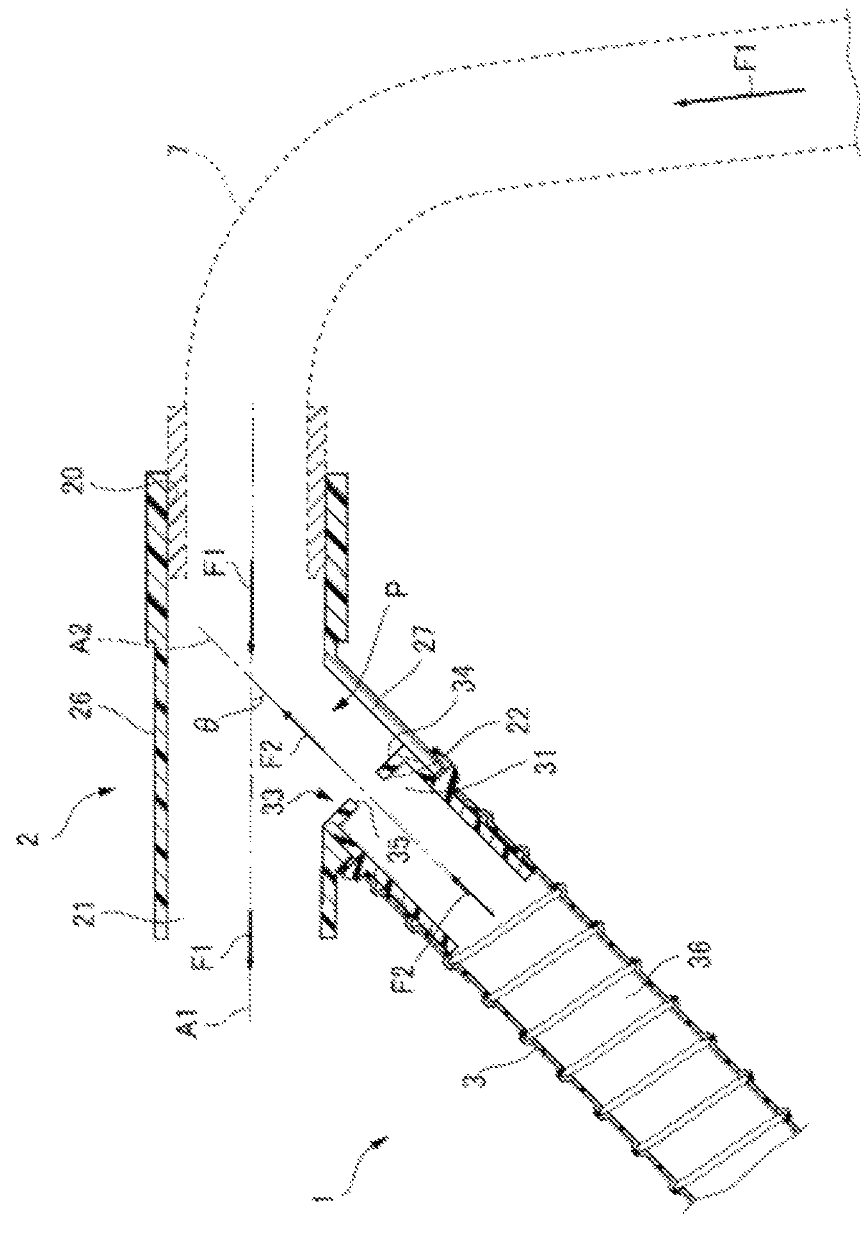
FIG. 3 is a view illustrating a longitudinal section of a tracheal connector body.

The respiratory-side tube portion 27 is obliquely connected to the exhaust-side tube portion 26. Specifically, as illustrated in FIG. 3, an axial direction A1 of the exhaust-side tube portion 26 extends obliquely with respect to an axial direction A2 of the respiratory-side tube portion 27. An angle $\theta$ between the axial direction A1 and the axial direction A2 is, for example, within a range of 35° to 55°. The internal space of the respiratory-side tube portion 27 and the internal space of the exhaust-side tube portion 26 communicate with each other. The two internal spaces communicating with each other form a respiratory gas flow path P that allows the respiratory gas to flow therein.

The connector tube 3 is connected to the tracheal connector body 2 and the gas tube 6 of the respiratory gas generator 5. As illustrated in FIG. 2, the connector tube 3 may include a first connection end 31, a second connection end 32, and a tube body 36. The first connection end 31 is connected to the respiratory port 22. The second connection end 32 is located on the side opposite to the first connection end 31, and is connected to the gas tube 6 of the respiratory gas generator 5 (see FIG. 1). The tube body 36 extends between the first connection end 31 and the second connection end 32, and is formed in a bellows shape.

As illustrated in FIG. 3, the first connection end 31 is provided with a restriction mechanism 33. The restriction mechanism 33 is configured to narrow the respiratory gas flow path P that allows the respiratory gas to flow therein so that a flow of the respiratory gas is restricted and accelerated. The restriction mechanism 33 may include a closing plate 34 configured to close a part of the opening of the first connection end 31, and a through orifice 35 formed in the closing plate 34. The closing plate 34 may be formed integrally with the first connection end 31. The closing plate 34 blocks the flow of the respiratory gas (hereinafter, the inspiratory flow F2) supplied from the respiratory gas generator 5, while the through orifice 35 allows the inspiratory flow F2 to pass therethrough. In this way, the respiratory gas flow path P can be narrowed by the closing plate 34 and the through orifice 35.

Figure 4:
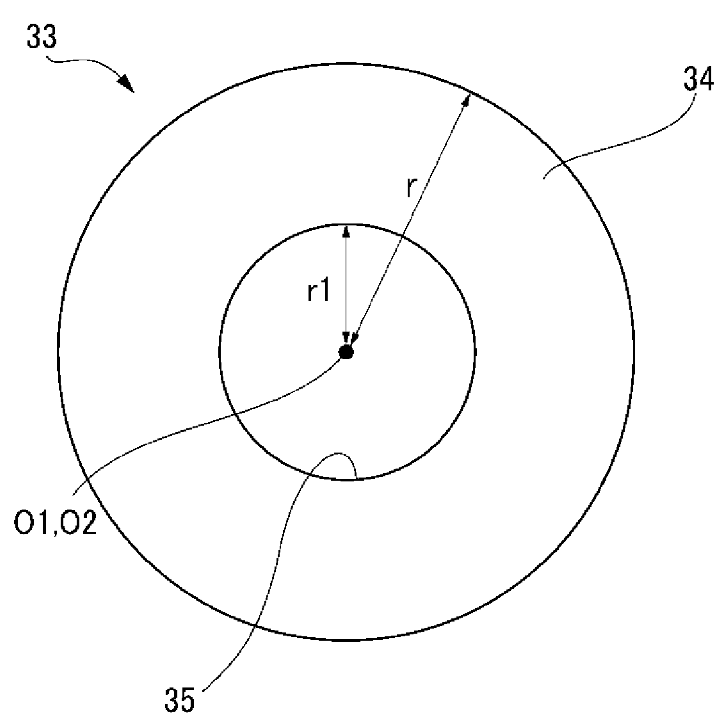
FIG. 4 is a plan view of a restriction mechanism provided in the connector tube.

As illustrated in FIG. 4, in a plan view, the closing plate 34 and the through orifice 35 are formed in circular shapes. A center point O1 of the closing plate 34 and a center point O2 of the through orifice 35 may substantially coincide with each other. The ratio of the surface area of the closing plate 34 to the flow path cross-sectional area of the connector tube 3 at the first connection end 31 may be, for example, in a range of 75% to 90%. For example, when the ratio of the surface area of the closing plate 34 to the flow path cross-sectional area is 75%, the ratio of the opening area of the through orifice to the flow path cross-sectional area is 25%. In this case, since the flow path cross-sectional area is four times the opening area of the through orifice, a radius r1 of the through orifice 35 is ½ of the flow path cross-sectional radius r.

When the ratio of the surface area of the closing plate 34 to the flow path cross-sectional area is 75% to 90%, the narrowing ratio of the respiratory gas flow path P achieved by the restriction mechanism 33 is also in the range of 75% to 90%. That is, when the ratio of the surface area of the closing plate 34 to the flow path cross-sectional area is N %, the narrowing ratio of the respiratory gas flow path P achieved by the restriction mechanism 33 is also in the range of N %. In this example, the restriction mechanism 33 is provided at the first connection end 31, but the place where the restriction mechanism 33 is formed is not particularly limited. For example, the restriction mechanism 33 may be formed integrally with the respiratory-side tube portion 27. In this case, same or similarly, the restriction mechanism 33 is formed on the respiratory gas flow path P between the respiratory port 22 and the tracheal port 20.

According to the present embodiment, since the restriction mechanism 33 configured to narrow the respiratory gas flow path P is provided on the respiratory gas flow path P (specifically, the first connection end 31 of the connector tube 3) between the respiratory port 22 and the tracheal port 20, the inspiratory flow F2 is narrowed by the restriction mechanism 33. Further, when an inspiratory flow F2 passing through the restriction mechanism 33 collides with the flow of the expired air of the patient U passing through the tracheal port 20 (hereinafter referred to as an expiratory flow F1), a turbulent flow region is formed in the vicinity of the tracheal port 20. Therefore, the expiratory flow F1 is less likely to flow smoothly toward the side closer to the exhaust port 21, and thus the pressure in the vicinity of the tracheal port 20 increases.

As a result, the value of the dynamic PEEP (positive end expiratory pressure) dramatically increases. Further, the restriction mechanism 33 is not provided on the side closer to the exhaust port 21. Therefore, the restriction mechanism 33 can suitably prevent the expired air of the patient U from being not sufficiently discharged into the atmosphere. For example, in the case where the restriction mechanism 33 is provided on the side closer to the exhaust port 21, it is assumed that the phlegm or the like of the patient U included in the expired air blocks the through orifice 35 of the restriction mechanism 33. The present embodiment, however, can suitably prevent such situation. Therefore, it is possible to provide the tracheal connector 1 capable of suitably preventing insufficient discharge of the expired air of the patient U into the atmosphere while dramatically improving the value of the dynamic PEEP of the patient U. Furthermore, by dramatically improving the dynamic PEEP of the patient U, the wearing period of the respirator of the patient U can be shortened.

Further, in the present embodiment, the narrowing ratio of the respiratory gas flow path P achieved by the restriction mechanism 33 is set within the range of 75% to 90%. Therefore, the respiratory gas supplied from the respiratory gas generator 5 can be reliably red into the respiratory tract of the patient U, and the value of the dynamic PEEP can be dramatically increased. In this regard, when the narrowing ratio of the respiratory gas flow path P exceeds 90%, the value of the dynamic PEEP increases, and the pressure around the restriction mechanism 33 excessively increases. On the other hand, when the narrowing ratio of the respiratory gas flow path P is less than 75%, it is difficult to dramatically increase the value of the dynamic PEEP.

In the present embodiment, the angle θ between the axial direction A1 of the exhaust-side tube portion 26 and the axial direction A2 of the respiratory-side tube portion 27 is, for example, within a range of 35° to 55°. Thereby, it is possible to dramatically increase the value of the dynamic PEEP while eliminating the degree of variation in the value of the dynamic PEEP of patients U having various respiratory disorders. In this regard, as the angle θ between the axial direction A1 and the axial direction A2 is smaller, the expiratory flow F1 is less likely to smoothly flow toward the exhaust port 21, and thus the value of the dynamic PEEP tends to increase. On the other hand, as the angle θ is smaller, the degree of variation in the value of the dynamic PEEP between patients increases. Therefore, in consideration of the degree of variation in the dynamic PEEP value between patients, the angle θ is preferably in the range of 350 to 550.

The embodiment of the presently disclosed subject matter is described above. However, the technical scope of the presently disclosed subject matter should not be construed as being limited to the description of the embodiment. It is understood by those skilled in the art that the present embodiment is an example and various modifications can be made within the scope of the inventions described in the claims. The technical scope of the presently disclosed subject matter should be determined based on the scope of the invention described in the claims and the scope of equivalents thereof.

For example, in the restriction mechanism 33 according to the present embodiment, the concentric single through orifice 35 is formed in the closing plate 34, but the position, the number, and the shape for forming the through orifice 35 are not particularly limited. For example, two or more through orifices may be formed at any position on the closing plate 34. Further, the shape of the through orifice 35 may be a polygon (for example, a triangular shape or a quadrangular shape). In this way, the configuration of the restriction mechanism 33 illustrated in the present embodiment is not particularly limited.

What is claimed is:

1. A tracheal connector connected to a respiratory gas generator configured to supply a respiratory gas to a subject and a tracheal tube inserted into a trachea of the subject, wherein the tracheal connector comprising:

a tracheal connector body connected to the tracheal tube;

a connector tube connected to the tracheal connector body and the respiratory gas generator;

a respiratory gas flow path configured to flow the respiratory gas in the respiratory gas flow path; and a restriction mechanism configured to narrow the respiratory gas flow path so that a flow of the respiratory gas is restricted and accelerated, the tracheal connector body comprising:

a tracheal port connected to the tracheal tube;

an exhaust port facing the tracheal port and configured to discharge at least expired air of the subject; and a respiratory port connected to the connector tube, wherein the restriction mechanism is provided on the respiratory gas flow path between the respiratory port and the tracheal port;

the connector tube includes:

a first connection end connected to the respiratory port; and a second connection end located on a side opposite to the first connection end and connected to the respiratory gas generator, and the restriction mechanism is provided at the first connection end.

2. The tracheal connector according to claim 1, wherein the restriction mechanism includes:

a closing plate configured to close a part of an opening of the first connection end; and at least one through orifice formed in the closing plate.

3. The tracheal connector according to claim 2, wherein a ratio of a surface area of the closing plate to a flow path cross-sectional area of the connector tube at the first connection end is in a range of 75% to 90%.

4. The tracheal connector according to claim 1, wherein a narrowing ratio of the respiratory gas flow path achieved by the restriction mechanism is in a range of 75% to 90%.

5. The tracheal connector according to claim 1, wherein the tracheal connector body includes:

an exhaust-side tube portion extending between the tracheal port and the exhaust port; and a respiratory-side tube portion connected to the exhaust-side tube portion and including the respiratory port, an axial direction of the respiratory-side tube portion extends obliquely with respect to an axial direction of the exhaust-side tube portion, and an angle between the axial direction of the respiratory-side tube portion and the axial direction of the exhaust-side tube portion is in a range of 35° to 55°.

* * * * *